(12) United States Patent
Callahan et al.

(10) Patent No.: US 6,666,887 B1
(45) Date of Patent: Dec. 23, 2003

(54) DEFORMABLE INTRAOCULAR MULTI-FOCUS LENS

(75) Inventors: Wayne B. Callahan, Abingdon, VA (US); Jeffery Scott Callahan, Blountville, TN (US)

(73) Assignee: ThinOptX, Inc., Abingdon, VA (US)

( * ) Notice: Subject to any disclaimer, the term of this patent is extended or adjusted under 35 U.S.C. 154(b) by 26 days.

(21) Appl. No.: 10/058,978

(22) Filed: Oct. 22, 2001

Related U.S. Application Data

(60) Provisional application No. 60/242,128, filed on Oct. 20, 2000.

(51) Int. Cl.$^7$ .................................................. A61F 2/06
(52) U.S. Cl. ...................................... 623/6.25; 623/6.28
(58) Field of Search ............................... 623/6.24, 6.25, 623/6.26–6.31

(56) References Cited

U.S. PATENT DOCUMENTS

| | | |
|---|---|---|
| 4,254,509 A | 3/1981 | Tennant |
| 4,435,855 A | 3/1984 | Pannu |
| 4,573,998 A | 3/1986 | Mazzocco |
| 4,585,456 A | 4/1986 | Blackmore |
| 4,624,669 A | 11/1986 | Grendahl |
| 4,655,775 A | 4/1987 | Clasby, III |
| 4,769,035 A | 9/1988 | Kalman |
| 4,795,462 A | 1/1989 | Grendahl |
| 4,816,032 A | 3/1989 | Hetland |
| 4,923,296 A | 5/1990 | Erickson ........................ 351/161 |
| 4,932,970 A * | 6/1990 | Portney ........................ 623/6.25 |
| 4,950,290 A | 8/1990 | Kamerling |
| 4,994,080 A | 2/1991 | Shepard |
| 4,995,714 A * | 2/1991 | Cohen ........................... 351/161 |
| 5,002,568 A | 3/1991 | Katzen |
| 5,019,098 A | 5/1991 | Mercier ............................... 623/6 |
| 5,076,684 A | 12/1991 | Simpson et al. |
| 5,098,444 A | 3/1992 | Feaster |
| 5,100,226 A | 3/1992 | Freeman |
| 5,166,711 A | 11/1992 | Portney |
| 5,229,797 A | 7/1993 | Futhey et al. |
| 5,258,025 A | 11/1993 | Fedorov et al. |
| 5,480,428 A | 1/1996 | Fedorov et al. |
| 5,522,890 A | 6/1996 | Nakajima et al. |
| 5,628,794 A | 5/1997 | Lindstrom |
| 5,682,223 A | 10/1997 | Menezes et al. |
| 5,782,911 A | 7/1998 | Herrick |
| 5,800,532 A | 9/1998 | Lieberman |
| 5,855,605 A | 1/1999 | Herrick |
| 5,919,229 A | 7/1999 | Portney |
| 6,090,141 A | 7/2000 | Lindstrom |
| 6,096,077 A | 8/2000 | Callahan et al. |
| 6,120,148 A | 9/2000 | Fiala et al. |
| 6,277,146 B1 | 8/2001 | Peyman et al. ............ 623/6.17 |

* cited by examiner

*Primary Examiner*—Corrine McDermott
*Assistant Examiner*—Hieu Phan
(74) *Attorney, Agent, or Firm*—Waddey & Patterson, P.C.; Douglas W. Schelling

(57) ABSTRACT

An intraocular corrective lens, comprising an optical portion having a normal shape constructed of a material which is biologically compatible with the natural lens of the eye and for positioning anterior thereof, or in replacement thereof; said optical portion also having an anterior convex lenticular surface and a posterior surface, wherein said posterior surface comprises a central disk which is radially surrounded by a series of annular rings, said central disk and said series of annular rings forming a series of radial steps along said posterior surface; wherein said posterior surface and said anterior lenticular surface have a minimum separation of 0.025 mm and a maximum separation of 0.1 mm; the central disk being of one diopter power and at least one annular ring is of a second diopter power; and at least one anchor attached to said optical portion for anchoring said optical portion anteriorly to the natural lens of the eye.

29 Claims, 2 Drawing Sheets

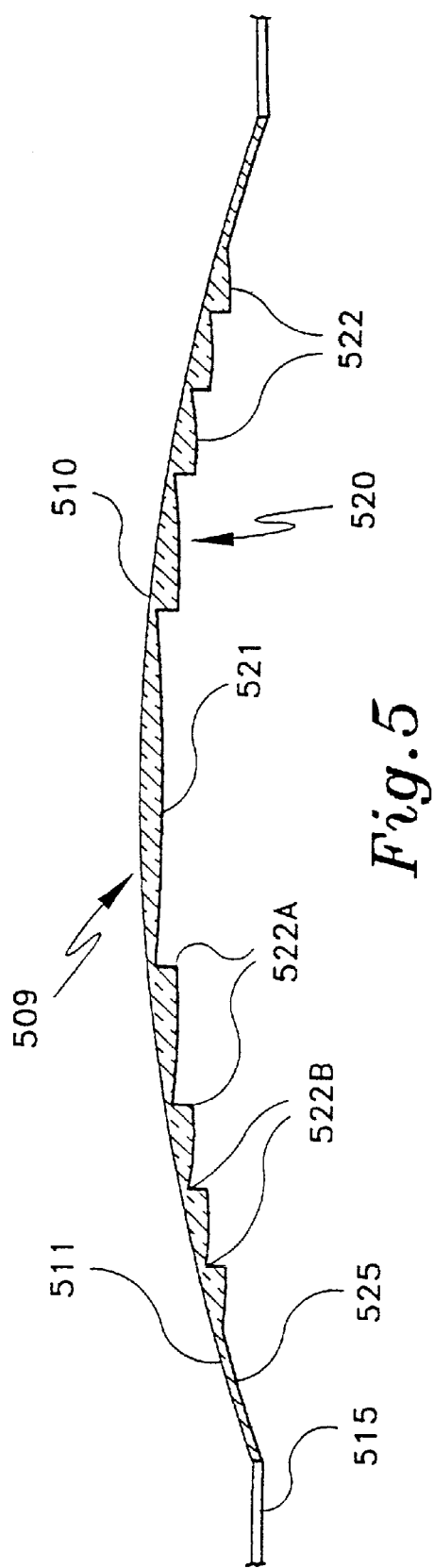
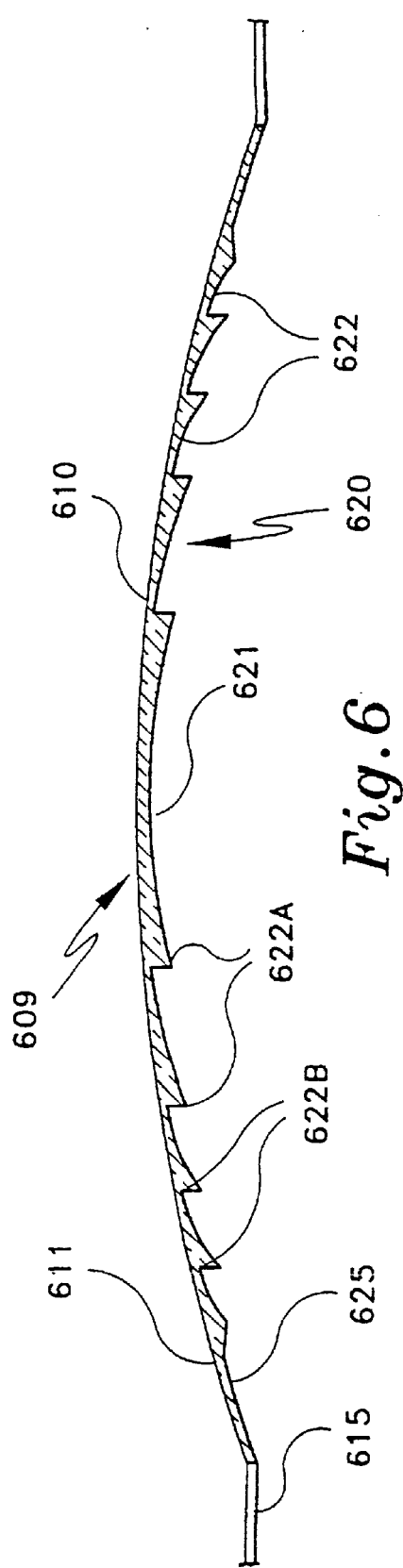

DEFORMABLE INTRAOCULAR MULTI-FOCUS LENS

This application claims priority to Provisional Application Ser. No. 60/242,128 filed on Oct. 20, 2000, entitled "Deformable Intraocular Multi-focal Lens", which is incorporated herein by reference in its entirety.

BACKGROUND OF THE INVENTION

1. Field of the Invention

The present invention relates to a deformable intraocular implantable refractive lens to correct vision problems, which lens is inserted into the eye anterior to the natural lens and has a functional design which minimizes cutting or stretching of the cornea to do so. The lens of the present invention may be multifocal to treat presbyopia.

2. Description of the Related Art

Doctors trained in ophthalmology routinely surgically extract cataract-impaired lenses from patients' eyes and subsequently implant artificial lenses to prevent blindness. The artificial lens is typically manufactured from polymethylmethacrylate (PMMA), an acrylic plastic. PMMA is a preferred material because it is biologically compatible with the tissue of the eye, and it does not degrade over time.

Over the last 50 years, the success rate for implanting these intraocular lenses has improved to the point that surgeons now want to implant intraocular implantable refractive lenses anterior to the natural lenses to correct common vision problems, such as myopia (near-sightedness), hypermetropia (far-sightedness), and astigmatism (aberration in the convexity of the optic lens or cornea). In order to insert an intraocular lens, an incision of approximately 10 mm is made through the cornea or sclera. The new lens is passed through the incision into the anterior chamber of the eye. The inserted lens is then positioned over the pupil and anchored either anteriorly to or posteriorly from the iris. Unfortunately, the making of the incision has been known to cause astigmatism of the cornea.

Experience from cataract surgeries shows that the astigmatism will be reduced if a smaller incision is made. It follows that if the lens could be manipulated through a smaller incision, it will reduce the severity of the astigmatism. The optical portion of the intraocular lens, though, must have a diameter of at least approximately 6 mm in order to properly cover the pupil. So, the only way to pass a lens through a smaller incision is to first fold the lens into a u-shape or roll it so that the opposite edges are overlapping. However, currently designed PMMA lenses are rigid and too brittle to be rolled or folded. While it is known that a material which is rigid at a given thickness may be flexible at a lesser thickness, the maximum material thickness under which PMMA is flexible is approximately 0.25 mm. This thickness is too thin for use in a conventional implantable refractive lens because of the lens' optics requirements.

A lens has a convex lenticular surface into which incident light passes. The lens also has a posterior surface, opposite the lenticular surface, from which the refracted light exits. The posterior surface may be convex, planar or concave. The power of the lens is determined by the curvature of the lenticular and posterior surfaces. Because the optical portion of the implantable refractive lens is approximately 6 mm wide and the thickest portion is at the center of the lens, a conventional lens having a maximum thickness of under 0.25 mm at its center in order to be rolled may possess the requisite curvature to be optically useful.

Alternative lens materials are also currently used for the replacements of the natural lenses of cataract patients. One such alternative lens material is an acrylic that has a lower molecular weight than PMMA. This lower-weight acrylic lens is softer than PMMA so it can be folded in a u-shape. However, if not handled very carefully, the lower-weight acrylic will crease, rendering it unusable. In addition, the material is soft enough to adhere to itself if it is rolled or folded far enough to allow overlapping. The multifocal lens of the present invention can be inserted "flat" (i.e., not folded) if the lens is too thick to be folded.

Another alternative lens material is silicone, the same material that is sometimes used in breast implants. The silicone collects protein in some patients, giving a yellow appearance and reducing the passage of light. The protein can become so dense as to create the appearance of a secondary cataract, significantly reducing the patient's ability to see. This is usually a lesser concern for cataract patient, when compared to the blindness, which would result from the cataract. Also, most cataract patients tend to be elderly so the protein build-up might not advance too far during their lifetimes. For some cataract patients, though, the protein build-up necessitates that the silicone lens be removed and replaced. Because of the problems associated with protein build-up, silicone is preferably not used to make long-term intraocular implantable refractive lenses for implantation into younger persons.

Two inventions for a deformable intraocular lens are set forth in U.S. Pat. No. 4,573,998 issued March 1986, to Mazzocco; and U.S. Pat. No. 5,522,890 issued June 1996, to Nakajima et al. These inventions employ a lens made of a molded elastic material. They do not disclose or suggest the use of PMMA.

Other inventions generally related to the art of optical lenses include: U.S. Pat. No. 4,254,509 issued March 1981, to Tennant (Accommodating Intraocular a Implant); U.S. Pat. No. 4,585,456 issued April 1986, to Blackmore (Corrective Lens For The Natural Lens Of The Eye); U.S. Pat. No. 4,655,775 issued April 1987, to Clasby (Intraocular Lens With Ridges); U.S. Pat. No. 4,769,035 issued September 1988, to Kelman (Artificial Lens And The Method For Implanting Such Lens); U.S. Pat. No. 4,795,462 issued January 1989, to Grendahl (Cylindrically Segmented Zone Of Focus Artificial Lens); U.S. Pat. No. 4,816,032 issued March 1989, to Hetland (Arrangement In An Intraocular Anterior Chamber Lens); U.S. Pat. No. 4,950,290 issued August 1990, to Kamerling (Posterior Chamber Intraocular Lens); U.S. Pat. No. 4,994,080 issued February 1991, to Shepard (Optical Lens Having At Least One Stenopaeic Opening Located In The Central Area Thereof); U.S. Pat. No. 5,076,684 issued December 1991, to Simpson et al. (Multi-Focal Diffractive Ophthalmic Lenses); U.S. Pat. No. 5,098,444 issued March 1992, to Feaster (Epiphakic Intraocular Lens And Process Of Implantation); U.S. Pat. No. 5,166,711 issued November 1992, to Portney (Multifocal Ophthalmic Lens); U.S. Pat. No. 5,229,797 issued July 1993, to Futhey et al. (Multifocal Diffractive Ophthalmic Lenses); U.S. Pat. No. 5,258,025 issued November 1993, to Fedorov et al. (Corrective Intraocular Lens); U.S. Pat. No. 5,480,428 issued January 1996, to Fedorov et al. (Corrective Intraocular Lens). None of these inventions solves the above-disclosed problems associated with currently known deformable intraocular lenses.

Regarding multifocal lens, U.S. Pat. No. 5,800,532 to Lieberman discloses an intraocular lens that has a central portion having a first refractive power region and a peripheral portion having a second refractive power region. The second refractive power region is substantially concentrated only in one predetermined location; or is asymmetrically disposed on the inferior nasal quadrant of the intraocular lens.

U.S. Pat. Nos. 5,782,911 and 5,855,605 to Herrick disclose a multifocal lens system that includes a first optical lens having a predetermined diopter power and a second lens having a predetermined diopter power positioned eccentrically inferior of the first lens for receiving light rays from a distant object.

U.S. Pat. No. 5,628,794 to Lindstrom discloses a corneal implant lens which provides multifocal capability for the correction of presbyopia and ametropia and is coated with a hydrogel material.

U.S. Pat. No. 6,090,141 discloses an intracorneal lens that is inserted between the stromal layer of a cornea of an eye, and provides two regions of focality.

U.S. Pat. No. 5,682,223 to Menezes et al. discloses a multifocal annular ring lens comprising a central area with a circular disc, a plurality of annular rings having alternating spherical powers.

U.S. Pat No. 5,919,229 to Portney discloses a multifocal opthalmic lens having outer annular zones with vision correction powers less than a far vision correction power of the patient.

U.S. Pat. No. 6,120,148 to Fiala et al. discloses muiltifocal diffractive lens with a stepped design. The lens comprises at least two annular zones A need exists for a deformable intraocular implantable refractive lens which requires a minimal incision through the cornea, but does not possess the drawbacks associated with the currently known, alternative lens materials.

Furthermore, a need exists for a multifocal lens that allows for the treatment of presbyopia and other conditions. Presbyopia is a condition, typically of middle age, where the lens of the eye reduces or eliminates accommodation and ability to focus on near objects. The lens of the present invention allows for treatment of presbyopia and provides a multifocal lens.

None of the above inventions and patents, taken either singularly or in combination, is seen to describe such a lens as is achieved by the instant invention as claimed.

SUMMARY OF THE INVENTION

An object of the present invention is to provide an intraocular corrective lens, comprising an optical portion having a normal shape constructed of a material which is biologically compatible with the natural lens of the eye and for positioning anterior thereof. The optical portion may also have an anterior convex lenticular surface and a posterior surface, wherein the posterior surface comprises a central disk which is radially surrounded by a series of annular rings, forming a series of radial steps along said posterior surface; wherein said posterior surface and said anterior lenticular surface have a minimum separation of about 0.025 mm and a maximum separation of about 0.1 mm. The central disk may be of one diopter power and at least one annular ring is of a second diopter power. Finally, the lens of the present invention further comprises at least one anchor (i.e., haptics) attached to said optical portion for anchoring said optical portion anteriorly to the natural lens of the eye.

In another embodiment of the present invention, the optical portion of the corrective lens has a predetermined maximum thickness under which the material may be rolled without exceeding the elastic limit of the material, and a predetermined minimum thickness above which the material retains said normal shape. Therefore, the deformable intraocular corrective lens of this embodiment may be deformed for passage through a corneal incision having a length smaller than the diameter of the deformable intraocular corrective lens.

Preferably, the material forming said optical portion is polymethylmethacrylate (PMMA). Furthermore, the intraocular corrective lens of the present invention may optionally further comprise a transition area or stem disposed at the periphery of the optical portion, the anchor extending from the transition area. The transition area acts to support the haptics. Preferably, the haptic fingers extend from the transition area and sweep around the periphery the optical portion of the lens.

Preferably, the central disk is of one substantially constant diopter power and each annular ring is of a substantially constant diopter power. Preferably, the central disk is surrounded by 4 annular rings.

The present invention further relates to a deformable intraocular corrective lens, comprising:

a. an optical portion having a normal shape constructed of a material which is biologically compatible with the natural lens of the eye and for positioning anterior thereof, said optical portion having a predetermined maximum thickness of 0.25 mm under which the material may be rolled without exceeding the elastic limit of the material, said optical portion having a predetermined minimum thickness of 0.0125 mm above which the material retains said normal shape, whereby said deformable intraocular corrective lens is deformed for passage through a corneal incision having a length smaller than the diameter of the deformable intraocular corrective lens;

b. said optical portion also having an anterior convex surface and a posterior surface, wherein said posterior surface comprises a central disk which is radially surrounded by a series of annular rings, said central disk and said series of annual rings forming a series of radial steps along said posterior surface; whereby said posterior surface and said anterior lenticular surface having a maximum separation of 0.1 mm, and the central disk being of a first substantially constant diopter power and at least one annular ring is of a second substantially constant diopter power; and c. and anchor anchoring said optical portion anteriorly to the natural lens of the eye.

The present invention further relates to an intraocular corrective lens, comprising: an optical portion having a normal shape constructed of a material which is biologically compatible with the natural shape of the eye that includes a central optic radially surrounded by at least one annular ring, radial steps defining said annular rings; and a pair of haptic fingers to anchor the optical portion in a eye.

Finally, the present invention relates to a method of correcting a cause of impaired vision, comprising the steps of:

a. making an incision for access to the anterior chamber of an eye having a length of about 4 mm or less;

b. providing a corrective lens formed of polymethylmethacrylate material having a thickness of about 0.25 mm or less, having a diameter of 6 mm., said optical portion also having an anterior convex surface and a posterior surface, wherein said posterior surface comprises a central disk which is radially surrounded by a series of annular rings, said central disk and said series of annual rings forming a series of radial steps along said posterior surface; whereby said posterior surface and said anterior lenticular surface having a maximum separation of 0.1 mm, and the central disk being of a first diopter power and at least one annular ring is of a second diopter power c. integrally providing support haptics for anchoring the corrective lens;

d. rolling the corrective lens and the support haptics without exceeding the elastic limit of the polymethylmethacrylate material into a rolled package;

e. inserting the rolled package into the anterior chamber of the eye via the incision;

f. unrolling the rolled package internally of the anterior chamber;

g. anchoring the haptics anteriorly of the lens of the eye in the anterior chamber;

h. repairing the incision made in the eye.

BRIEF DESCRIPTION OF THE DRAWINGS

FIG. 5 is a cross-sectional fragmented view of a second embodiment of the invention.

FIG. 6 is a cross-sectional fragmented view of a third embodiment of the invention.

Similar reference characters denote corresponding features consistently throughout the attached drawings.

DETAILED DESCRIPTION OF THE INVENTION

Figure 1:
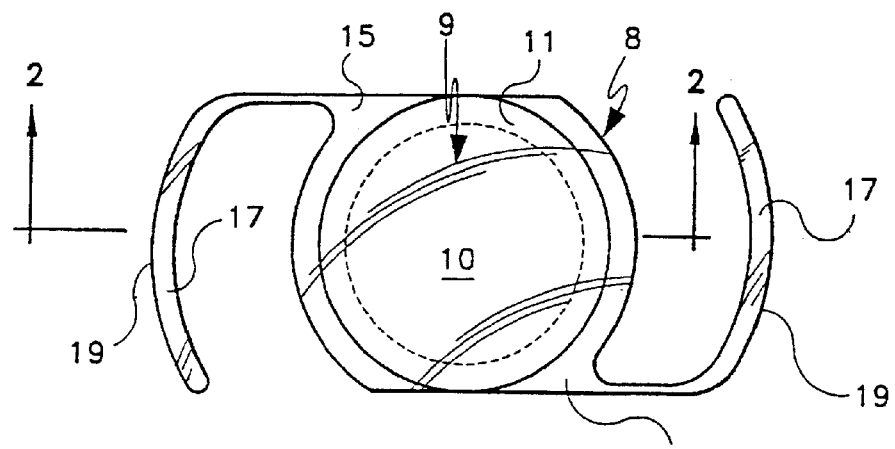
FIG. 1 is a top view of a deformable intraocular implantable refractive lens according to the present invention.

The present invention is a deformable intraocular implantable refractive lens that may preferably be constructed from PMMA for rolled or folded insertion into the human eye to correct common vision problems. The lens of the present invention may be deformable because all portions of the lens are manufactured to a thickness which is within a predetermined range of thicknesses. More particularly, at the first end of the range, the thickness of the lens is less than a maximum material thickness, the threshold under which the lens is flexible. At the second end of the range, the thickness of the lens is also greater than a minimum material thickness, the threshold above which the lens material will retain its pre-flexed shape subsequent to flexing. The novel design also enables the deformable lens to possess any desired convexity or concavity which would be required for vision correction.

As stated above, preferably the lens is constructed from PMMA. However, the deformable lens of the present invention may also be constructed from any other biologically compatible material that can be manufactured thinner than a pre-determined maximum material thickness to be rolled or folded for passage through a small incision in the cornea or sclera if such a method of insertion is desired for the lens of the present invention. For example, the lens of the present invention may be constructed from silicone, acrylic, and hydrogel.

The Hardcourt Academic Press Dictionary of Science and Technology defines hydrogel as a gel whose liquid constituent is water. The Plastics Technology Handbook, Third Edition, Revised and Expanded by Manas Chanda and Salil K. Roy, page 584 states "Mention may also be made here of the 2-hydroxyethyl ester of methacrylic acid, which is the monomer used for soft contact lenses. Co-polymerization with ethylene glycol dimethacrylate produces a hydrophilic network polymer (a hydrogel). Hydrogel polymers are brittle and glassy when dry but become soft and plastic on swelling in water." Hydrogel is described as a polymer that absorbs water.

Typically, in some cases the non-PMMA materials will have to be thicker, but they can still have the rings of the present invention and be significantly thinner that a standard lens made with the same material.

Additionally, embodiments of the lens of the present invention may be inserted as a flat lens when a thicker lens (i.e., nondeformable lens) is required for certain conditions such as cataract treatments.

The improved lens may replace the need for spectacles, implantable refractive lenses or radial keratotomy.

The intraocular implantable refractive lens has an anterior convex lenticular surface. The posterior surface of the lens comprises a planar, central disk or central optic which is surrounded by a series of concentric, planar, annular rings or step rings. The step rings may be of increasing diameter. The annular rings are parallel to each other and to the central disk. The central disk and annular rings are also perpendicular to a radial axis passing though the apex of the lenticular surface. In combination, the central disk and the series of annular rings form a series of steps extending radially from the disk across the posterior surface to maintain a close proximity to the lenticular surface. Typically, the annular rings will number from 1 to 10, and preferably there are 4–6 annular rings. Most preferably, there are 4.

The central disk and the planer, annular rings may be a different diopter power to accommodate treatment of presbyopia and other conditions. In such an embodiment, the center ring focuses on a first point, and one or more outer annular rings have a higher or lower power to focus on at least a second point. That is, the central disk is of one diopter power and at least one annular ring is of a second diopter power. Preferably, the diopter power is substantially constant about the central disk or annular ring.

In other embodiments, at least one annular ring is of a predetermined concavity for obtaining a second focusing power. Additionally, in other embodiments, at least one annular ring is of a predetermined convexity for obtaining a second focusing power.

Additionally, the annular rings may be planar, parallel to each other, and perpendicular to a radial axis passing though the apex of the lenticular surface and the central disk is of a predetermined convexity for obtaining a first particular power. Also, the annular rings may be planar, parallel to each other, and perpendicular to a radial axis passing through the apex of the lenticular surface and the central disk is of a predetermined concavity for obtaining a first particular power.

In other embodiments, the central disk may be of a predetermined concavity for obtaining a first particular focusing power and at least one annular ring is of a predetermined concavity for obtaining a second particular focusing power. Furthermore, the central disk may be of a predetermined convexity for obtaining a first particular focusing power and at least one annular ring is of a predetermined concavity for obtaining a second particular focusing power.

Additionally, central disk may be plano, or flat for obtaining a first particular power, and at least one annular ring may be of a predetermined convexity for obtaining a second particular focusing power. Also, the central disk may be of a predetermined convexity for obtaining a first particular power, and at least one annular ring may be plano for obtaining a second particular focusing power.

The thickness of the lens between the central disk of the posterior surface and the apex of the lenticular surface must be less than a predetermined maximum thickness. The predetermined maximum thickness is the thickness under which the material may be rolled or folded without exceeding the elastic limit of the selected lens material, except with respect to additional embodiments of the present invention where thicker lens are inserted flat for the treatment of cataracts, as discussed below. For a deformable lens constructed of PMMA, the maximum thickness between the posterior surface and the apex of the lenticular surface should be less than or equal to 0.25 mm.

Preferably, the thickness of the lens at the periphery of the central disk should be greater than a pre-determined minimum thickness. The predetermined minimum thickness is preferably the thickness above which the lens material will retain its pre-flexed shape subsequent to flexing. The minimum thickness is determined by the manufacturing process and the strength of the lens material. For the rollable or deformable PMMA lens of the present invention, a typical minimum thickness between the lenticular surface and the periphery of the central disk should be greater than or equal to 0.0125 mm. A typical maximum thickness is about 0.250 mm. For a flat, rigid PMMA lens of the present invention, a typical minimum thickness is about 0.0125 mm. For a flat, rigid PMMA lens of the present invention, a typical maximum thickness is a about 1.0 mm or more. A thinner lens is preferred, but it is not uncommon for a cataract lens to exceed 1 mm in thickness.

For silicone and acrylic materials, a typical minimum thickness is less than about 0.1 mm and a typical maximum thickness is about 1.0 mm or greater. As with the PMMA embodiments, a thinner lens is preferred.

With respect to the preference to a thinner cataract lens, in comparison, a typical cataract lens with a maximum thickness of 1.00 mm would typically be inserted in a 3.0 to a 3.5 mm incision. By minimizing the thickness to, for example, 0.35 mm, the incision could be reduced to about 2.5 mm or less.

The radial width of the central disk of the posterior surface also falls within a predetermined range. The thicker the lens is at its apex, the farther the radial width may extend before the periphery of the central disk approaches the predetermined minimum thickness. The specific range of radial widths is determined by both the convexity of the lenticular surface and the thickness of the lens at its apex.

Similar to the central disk, the thickness between the lenticular surface and the posterior surface of the lens at the internal diameter of each annular ring should be less than or equal to the predetermined maximum thickness. The thickness between the lenticular surface and the posterior surface of the lens at the external diameter of each annular ring should be greater than or equal to the predetermined minimum thickness. The radial width of the annular rings will be within a predetermined range of lengths which is determined by the convexity of the lenticular surface and the thickness of the lens at the internal diameter of the annular ring. The greater the thickness of the lens at the internal diameter of the annular ring, the greater the radial length may be extended before the exterior diameter approaches the pre-determined minimum thickness.

If an imaginary line is drawn to connect the posterior surface's internal diameters of the annular rings and the center of the central disk, the imaginary line will form an arc or parabola; depending on the various thicknesses chosen. This imaginary line forms the effective posterior surface. By changing the thicknesses and widths of the central disk and annular rings, the effective posterior surface may be shaped as desired. This is particularly relevant for applications in which the implanted lens is implanted posterior from the iris, as further described below. This is because the effective posterior surface may thereby be constructed in a predetermined shape which enables the implanted lens to be properly rested against the anterior surface of the natural lens capsule.

In one alternate embodiment of the invention, the central disk and annular rings of the posterior surface are not planar. Rather, each surface of the central disk and annular rings is convex. In a second alternate embodiment of the invention, each surface of the central disk and annular rings is concave. Thereby, particular degrees of convexity or concavity of each section of the posterior surface may be chosen to further help obtain particular focusing powers for different lenses. Also, in any of these embodiments, the central portion and annular rings of the lens may be of a symmetric or asymmetric ovular shape for correction of astigmatisms.

As stated above, the lens may be arranged such that the central disk and at least one annular ring is a different power. Furthermore, each annular ring, or step ring, may be a different power one to the other. Typically, the annular rings or step ring will be of increasing higher powers. The rings are defined by a corresponding series of radial steps.

The periphery of the optical portion comprises a parallel lenticular area. The parallel lenticular area is of uniform thickness. The parallel lenticular area prevents the phenomenon known as edge effects which occurs if the optical portion of the lens does not adequately cover the periphery of the pupil. The edge effects are produced in various situations including when overhead lights are illuminated in low lighting situations, such as in roadway tunnels.

An anchor is attached to the optical portion to securely position the deformable intraocular refractive lens, anteriorly to the natural lens of the eye. The implantable refractive lens also has a non-optical transition area interconnecting the anchor device to the optical portion of the lens. The transition area has a thickness of approximately 0.025 mm. The anchor device typically comprises a pair of haptic fingers extending from the transition area and circumvolving the optical lens. The thickness of the haptic fingers is preselected to provide the optimal combination of strength and flexibility. Preferably, the thickness of each of the haptic finger is approximately 0.076 mm. The outer circumference of the haptic finger comprises the haptic edge. The haptic edge of the implanted lens is biased against the intraocular tissues. The thickness of the haptic edge is preselected to provide minimal stress to the eye tissues. Preferably, the thickness if the haptic edge is approximately 0.125 MM. Different style haptics known in the art may be used in connection with the multifocal lens of the present invention. That is, any anterior chamber or posterior chamber lens that has haptics may be used in connection with the multi-focal lens of the present invention. For example, the stem/support anchors or haptics of U.S. Pat. No. 6,224,628 may be used in connection with the lens of the present invention. Also, the crossed anchors or haptics of U.S. Pat. No. 6,083,261 may be used.

If rolled and passed through the cornea, the implantable refractive lens may be placed in either of two selected positions. Specifically, the implanted lens may be positioned anterior to the iris, in the anterior chamber of the of eye. If this position is chosen, the haptic edge of each of the haptic fingers will be biased against the trabeculum. Once positioned and allowed to unroll, the implanted lens will return to its original shape.

In inserted flat, such as where a thicker lens is used for the treatment of cataracts, the lens may be inserted using procedures known in the art for inserting such types of lenses.

Alternatively, the implanted lens may be positioned posteriorly from the iris, and rest in front of the natural lens of the eye. If this position is chosen, the haptic edge of each of the haptic fingers will be biased against the zonulas or ciliary sulcus. The implanted lens is able to be placed posteriorly from the iris because of the thinness of the implanted lens. The lens' thinness provides adequate clearance between the natural lens when at rest and the posteriorly positioned, implanted lens. The biconvex natural lens is in its most curved position when at rest. Contraction of the zonulas places tension on the capsule, flattening the curvature of the natural lens. Thus, with the implanted lens in position, the natural lens will continue to have the ability to change shape, without the possibility of injury arising from contact with the implanted lens.

Alternatively, the lens of the present invention may be a replacement for the natural lens of the eye. In this embodiment the natural lens is removed from the capsule during cataract or clear lens extraction surgery. A lens of the present invention would placed in the capsule to replace the natural lens.

Accordingly, it is an object of the invention to provide a deformable intraocular refractive lens which requires a minimal incision through, or stretching of, the cornea for insertion.

It is another object of the invention to provide a deformable intraocular lens from a material such as PMMA which is biologically compatible with the eye tissue but will neither crease nor adhere to itself when rolled, nor cause eye disease as it ages.

It is a further object of the invention to provide an intraocular implantable refractive lens which may be positioned either anterior or posterior to the iris.

In another object of the invention is to provide an intraocular lens for correcting common vision problems, such as myopia, hypermetropia, and astigmatism.

Still another object of the present invention is a lens that is multifocal in that the central disk is a different power than at least one annular ring or step.

It is an object of the invention to provide improved elements and arrangements thereof in a deformable intraocular implantable refractive lens for the purposes described which is inexpensive, dependable and fully effective in accomplishing its intended purposes.

These and other objects of the present invention will become readily apparent upon further review of the following specification and drawings.

Turning now to the drawings, FIG. 1 is a top view of the deformable intraocular implantable refractive lens 8 according to the present invention. The deformable intraocular lens 8 is constructed of a material which is biologically compatible with the natural lens of the eye. The optical portion 9 of the lens 8 has an anterior convex lenticular surface 10. The periphery of the optical portion 9 comprises a parallel lenticular area 11. The parallel lenticular area 11 is of uniform thickness and is for preventing the phenomenon known as edge effects. A non-optical transition area 15 surrounds the parallel lenticular area 11. The anchor device extends from the transition area 15. In this embodiment, the anchor device comprises a pair of haptic fingers 17 circumvolving the optical portion 9 of the deformable intraocular implantable refractive lens 8. Each of the pair of haptic fingers 17 have an outer circumferential haptic edge 19 for biasing against the tissue of the eye.

Figure 2:
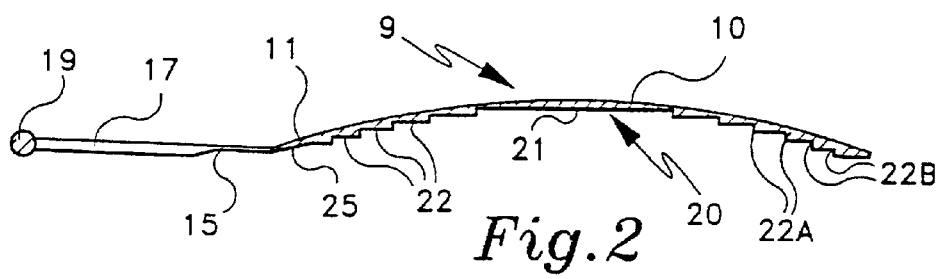
FIG. 2 is a cross-sectional view of the intraocular implantable refractive lens drawn along line 2—2.
Figure 3:
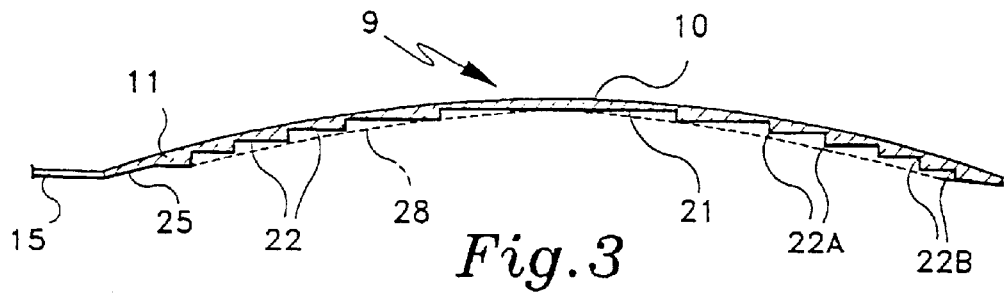
FIG. 3 is an enlarged, fragmented view of the optical portion and transition area of the lens depicted in FIG. 2.
Figure 4:
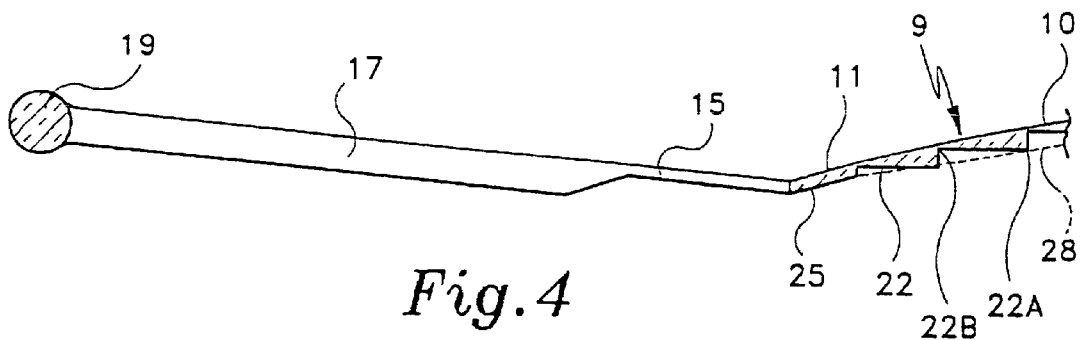
FIG. 4 is a fragmented view of the anchor and the transition area of the lens depicted in FIG. 2.

FIG. 2 is a cross-sectional view of the intraocular implantable refractive lens 8 drawn along line 2—2. FIG. 3 is a fragmented view of the optical portion 9 and transition area 15 of the lens 8 depicted in FIG. 2. FIG. 4 is a fragmented view of the anchor 16 and the transition area 15 of the lens depicted in FIG. 2. These three figures depict, to varying degrees, the anterior lenticular convex surface 10 of the optic portion 9. The posterior surface 20 is also depicted therein. The posterior surface 20 comprises a central disk 21 which is surrounded by a plurality of annular rings 22. The central disk 21 and series of annular rings 22 form a series of radial steps across the posterior surface 20 to maintain a close proximity to the lenticular surface 10. As discussed above, the central disk may be of one diopter power and at least one annular ring is of a second diopter power. Preferably, the diopter power is substantially constant about the central disk or ring. The thickness of the central disk 21 at the apex of the lenticular surface 10 is less than or equal to a predetermined maximum thickness so that the deformable intraocular implantable refractive lens 8 may be rolled without exceeding the elastic limit of the lens material. The thickness of the periphery of the central disk 21 is greater than or equal to a predetermined minimum thickness so that the deformable intraocular implantable refractive lens 8 will retain its pre-flexed shape subsequent to being rolled.

The surfaces of each annular ring 22 are planar and parallel with the central disk 21. Each annular ring 22 has an internal diameter 22A and an external diameter 22B. The thickness of the implantable refractive lens 8 between the internal diameter 22A of the posterior surface's 20 annular rings 22 and the lenticular surface 10 is less than or equal to the predetermined maximum thickness. The thickness of the implantable refractive lens 8 between the external diameter 22B of the posterior surface's 20 annular rings 22 and the lenticular surface 10 is greater than or equal to the predetermined minimum thickness. The outer most ring 22 is adjacent to the posterior surface 25 of the parallel lenticular area 11.

FIG. 3 further includes a dashed line 28 depicting an imaginary line which connects the center of the central disk 21 and the edges internal diameters 21A of the annular rings 22 of the posterior surface 20. The imaginary line depicted by dashed line 28 is the effective posterior surface of the optical portion 9 of the deformable intraocular implantable refractive lens 8.

FIG. 2 through FIG. 4 further depict the parallel lenticular area 11 surrounding the periphery of the optical portion 9. The parallel lenticular area 11 is of uniform thickness and is for preventing edge effects. The transition area 15 surrounds the parallel lenticular area 11. The anchor device extends from the transition area 15. FIG. 2 and FIG. 4 further depicts the anchor device. In this embodiment, the anchor device comprises a pair of haptic fingers 17 circumvolving the optical portion 9 of the deformable intraocular implantable refractive lens 8.

FIG. 5 is a cross-sectional fragmented view of a second embodiment of the invention. In this alternate embodiment, the anterior lenticular surface 510 of the optic portion 509 is of the same convex shape as in the previously described embodiment. The posterior surface 520 comprises a central disk 521 which is surrounded by a plurality of annular rings 522. The central disk 521 and series of annular rings 522 form a series of radial steps across the posterior surface 520 to maintain a close proximity to the lenticular surface 510.

In this embodiment, the surfaces of the central disk 521 and each of the annular rings 522 are convex. The thickness of the central disk 521 at the apex of the lenticular surface 10 is less than or equal to the predetermined maximum thickness. The thickness of the periphery of the central disk 521 is greater than or equal to a predetermined minimum thickness. The outermost ring 22 is adjacent to the posterior surface 25 of the parallel lentricular area 11.

Each annular ring 521 has an internal diameter 522A and an external diameter 522B. The thickness of the implantable refractive lens between the internal diameter 522A of the posterior surface's 520 annular rings 522 and the lenticular surface 510 is less than or equal to the predetermined maximum thickness. The thickness of the implantable refractive lens between the external diameter 522B of the posterior surface's 520 annular rings 522 and the lenticular surface 510 is greater than or equal to the predetermined minimum thickness. The parallel lenticular area 511 surrounds the periphery of the optical portion 509. The parallel lenticular area 511 is of uniform thickness. The transition area 515 surrounds the parallel lenticular area 511. The anchor device (not shown) extends from the transition area 515.

FIG. 6 is a cross-sectional fragmented view of a third embodiment of the invention. In this alternate embodiment, the anterior lenticular surface 610 of the optic portion 609 is of the same convex shape as in the previously described embodiments. The posterior surface 620 comprises a central disk 621 which is surrounded by a plurality of annular rings 622. The central disk 621 and series of annular rings 622 form a series of radial steps across the posterior surface 620 to maintain a close proximity to the lenticular surface 610.

In this embodiment, the surfaces of the central disk 621 and each of the annular rings 622 are concave. The thickness of the central disk 621 at the periphery of the central disk 621 is less than or equal to the predetermined maximum thickness. The thickness of the lens between the apex of the lenticular surface 610 and the central disk 621 is greater than or equal to a predetermined minimum thickness.

Each annular ring 621 has an internal diameter 622A and an external diameter 622B. The thickness of the implantable refractive lens between the internal diameter 622A of the posterior surface's 620 annular rings 622 and the lenticular surface 610 is greater than or equal to the predetermined minimum thickness. The thickness of the implantable refractive lens between the external diameter 622B of the posterior surface's 620 annular rings 622 and the lenticular surface 610 is less than or equal to the predetermined maximum thickness. The parallel lenticular area 611 surrounds the periphery of the optical portion 609. The parallel lenticular area 611 is of uniform thickness. The transition area 615 surrounds the parallel lenticular area 611. The anchor device (not shown) extends from the transition area 615. The outer most ring 22 is adjacent to the posterior surface 625 of the parallel lenticular area 611.

Other features of the invention will become apparent in the course of the following examples, which are given for illustration of the invention and are not intended to be limiting thereof.

EXAMPLE 1

This example is directed to a ring where the front, or anterior surface is fixed at a power of 10 diopter. In other embodiments, the power of the front diopter cam range from 1–15.

In this embodiment, the ring and the central optic diopter is the equivalent of the 10 diopter front in combination with the ring diopter. In other words, the two diopters are cumulative. In this embodiment, the center diopter in combination with the ring diopter has a 2.5 diopter correction.

Lenses of this example are as follows:

| Ring Diopter | Center Optic Diopter |
|---|---|
| 11 | 13.5 |
| 12 | 14.5 |
| 13 | 15.5 |
| 14 | 16.5 |

Lenses of this example include lenses with ring diopters of up to 30, and corresponding center optic diopter is 32.5. Rings of this example all have three annular rings, all of the same power.

EXAMPLE 2

This example is directed to rings of example 1, but which have a 3.5 diopter correction.

Lenses of this example are as follows:

| Ring Diopter | Center Optic Diopter |
|---|---|
| 11 | 14.5 |
| 12 | 15.5 |
| 13 | 16.5 |
| 14 | 17.5 |

Lenses of this example include lenses with ring diopters of up to 30, and corresponding center optic diopter is 33.5. Rings of this example have three annular rings, all of the same power.

EXAMPLE 3

This example is directed to rings of example 1, but have 4 annular rings.

EXAMPLE 4

This example is directed to rings of example 2, but have 4 annular rings.

EXAMPLE 5

This example is directed to rings of examples 1 and 2, having a 2.5 diopter correction, with examples being as follows:

| Ring Diopter | Center Optic Diopter |
|---|---|
| −35 | −32.5 |
| −20 | −17.5 |
| −10 | −7.5 |
| −1 | +1.5 |

EXAMPLE 6

This example is directed to rings of example 5, but have a 3.5 diopter correction.

All cited patents and publications referred to in this Application are herein expressly incorporated by reference.

The invention thus being described, it will be obvious that the same may be varied in many ways. Such variations are not regarded as a departure from the spirit and scope of the present invention, and all such modification as would be obvious to one of ordinary skill in the art are intended to be included within the scope of the following claims.

We claim:

1. An intraocular corrective lens, comprising:
    an optical portion having a normal shape constructed of a material which is biologically compatible with the natural lens of the eye and for positioning anterior thereof; said optical portion also having an anterior convex lenticular surface and a posterior surface, wherein said posterior surface comprises a central disk which is radially surrounded by a series of annular rings, said central disk and said series of annular rings forming a series of radial steps along said posterior surface; wherein said posterior surface and said anterior lenticular surface have a minimum separation of 0.025 mm and a maximum separation of 0.1 mm;
    the central disk being of one diopter power and at least one annular ring is of a second diopter power; and
    at least one anchor attached to said optical portion for anchoring said optical portion anteriorly to the natural lens of the eye or in place of the natural lens of the eye.

2. The intraocular corrective lens of claim 1, wherein said optical portion having a predetermined maximum thickness under which the material may be rolled without exceeding the elastic limit of the material, said optical portion having a predetermined minimum thickness above which the material retains said normal shape, whereby said deformable intraocular corrective lens is deformed for passage through a corneal incision having a length smaller than the diameter of the deformable intraocular corrective lens.

3. The intraocular corrective lens as defined in claim 2, wherein said material forming said optical portion is polymethylmethacrylate.

4. The intraocular corrective lens as defined in claim 2, wherein the annular rings are planar, parallel to each other, and perpendicular to a radial axis passing though the apex of the lenticular surface and the central disk is of a predetermined convexity for obtaining a first particular power.

5. The intraocular corrective lens as defined in claim 2, wherein the annular rings are planar, parallel to each other, and perpendicular to a radial axis passing through the apex of the lenticular surface and the central disk is of a predetermined concavity for obtaining a first particular power.

6. The intraocular corrective lens as defined in claim 2, wherein the central disk is of a predetermined convexity for obtaining a first particular power, and at least one annular ring is of a predetermined convexity for obtaining a second particular focusing power.

7. The intraocular corrective lens as defined in claim 2, wherein the central disk is of a predetermined concavity for obtaining a first particular focusing power and at least one annular ring is of a predetermined concavity for obtaining a second particular focusing power.

8. The intraocular corrective lens as defined in claim 2, wherein the central disk is of a predetermined convexity for obtaining a first particular focusing power and at least one annular ring is of a predetermined concavity for obtaining a second particular focusing power.

9. The intraocular corrective lens as defined in claim 2, wherein the central disk and annular rings are radially asymmetric for correcting astigmatisms.

10. The intraocular corrective lens as defined in claim 2, wherein the lens is sized for positioning anteriorly to the iris; and
    at least one anchor is sized for biasing against the anterior chamber angle of the eye.

11. The intraocular corrective lens as defined in claim 2, wherein
    the intraocular corrective lens is sized for positioning posterior to the iris, resting in front of the capsule of the natural lens of the eye; and
    at least one anchor is sized for biasing against the zonulas.

12. The intraocular corrective lens as defined in claim 2, further comprising a transition area disposed at the periphery of the optical portion, the anchor extending from the transition area.

13. The intraocular corrective lens as defined in claim 12, wherein the anchor device comprises a pair of haptic fingers extending from the transition area and circumvolving the optical portion of the deformable intraocular corrective lens, each of the pair of haptic fingers having an outer circumferential haptic edge for biasing against this tissue of the eye.

14. The intraocular corrective lens as defined in claim 2, wherein the optical portion further comprises a lenticular area at the periphery of the optical portion where the lenticular and posterior surfaces are parallel to one another for preventing edge effects.

15. The intraocular corrective lens of claim 2, the central disk being of one substantially constant diopter power and at least one annular ring is of a second substantially constant diopter power.

16. The intraocular corrective lens as defined in claim 2, wherein the central disk is of a predetermined concavity for obtaining a first particular power, and at least one annular ring is of a predetermined convexity for obtaining a second particular focusing power.

17. The intraocular corrective lens of claim 2, the central disk being of one substantially constant diopter power and at least one annular ring is of a second substantially constant diopter power and at least one annular ring is of a third substantially constant diopter power.

18. The intraocular corrective lens as defined in claim 2, wherein the central disk is plano for obtaining a first particular power, and at least one annular ring is of a predetermined convexity for obtaining a second particular focusing power.

19. The intraocular corrective lens as defined in claim 2, wherein the central disk is of a predetermined convexity for obtaining a first particular power, and at least one annular ring is plano for obtaining a second particular focusing power.

20. The intraocular corrective lens of claim 1, the central disk being of one substantially constant diopter power and at least one annular ring is of a second substantially constant diopter power.

21. The intraocular corrective lens of claim 1, the central disk being surrounded by 4 annular rings.

22. A deformable intraocular corrective lens, comprising:
    a. an optical portion having a normal shape constructed of a material which is biologically compatible with the natural lens of the eye and for positioning anterior thereof, said optical portion having a predetermined maximum thickness of 0.25 mm under which the material may be rolled without exceeding the elastic limit of the material, said optical portion having a predetermined minimum thickness of 0.0125 mm above which the material retains said normal shape, whereby said deformable intraocular corrective lens is deformed for passage through a corneal incision having a length smaller than the diameter of the deformable intraocular corrective lens;

b. said optical portion also having an anterior convex surface and a posterior surface, wherein said posterior surface comprises a central disk which is radially surrounded by a series of annular rings, said central disk and said series of annual rings forming a series of radial steps along said posterior surface; whereby said posterior surface and said anterior lenticular surface having a maximum separation of 0.1 mm, and the central disk being of a first substantially constant diopter power and at least one annular ring is of a second substantially constant diopter power; and c. and anchor anchoring said optical portion anteriorly to the natural lens of the eye.

23. The deformable intraocular lens of claim 22, wherein the annular rings are planar, parallel to each other, and perpendicular to a radial axis passing through the apex of the lenticular surface and the central disk is of a predetermined convexity for obtaining a first particular power.

24. The deformable intraocular lens of claim 22, wherein the annular rings are planar, parallel to each other, and perpendicular to a radial axis passing through the apex of the lenticular surface and the central disk is of a predetermined concavity for obtaining a first particular power.

25. The deformable intraocular corrective lens as defined in claim 22 wherein the central disk and annular rings are of a predetermined convexity for obtaining at least a particular first and second focusing power.

26. The deformable intraocular corrective lens as defined in claim 22 werein the central disk is of a predetermined convexity for obtaining a first particular focusing power and at least one annular ring is of a predetermined concavity for obtaining a second particular focusing power.

27. The deformable intraocular corrective lens as defined in claim 22, wherein the central disk and annular rings are of a predetermined concavity for obtaining a particular focusing power.

28. The deformable intraocular corrective lens as defined in claim 22, wherein the central disk and annular rings are radially asymmetric for correcting astigmatisms.

29. A method of correcting a cause of impaired vision, comprising the steps of:

a. making an incision for access to the anterior chamber of an eye having a length of about 4 mm or less;

b. providing a corrective lens formed of polymethylmethacrylate material having a thickness of about 0.25 mm or less, having a diameter of 6 mm., said optical portion also having an anterior convex surface and a posterior surface, wherein said posterior surface comprises a central disk which is radially surrounded by a series of annular rings, said central disk and said series of annual rings forming a series of radial steps along said posterior surface; whereby said posterior surface and said anterior lenticular surface having a maximum separation of 0.1 mm, and the central disk being of a first diopter power and at least one annular ring is of a second diopter power c. integrally providing support haptics for anchoring the corrective lens;

d. rolling the corrective lens and the support haptics without exceeding the elastic limit of the polymethylmethacrylate material into a rolled package;

e. inserting the rolled package into the anterior chamber of the eye via the incision;

f. unrolling the rolled package internally of the anterior chamber;

g. anchoring the haptics anteriorly of the lens of the eye in the anterior chamber;

h. repairing the incision made in the eye.

\* \* \* \* \*